United States Patent [19]

Berger et al.

[11] Patent Number: 5,268,306

[45] Date of Patent: Dec. 7, 1993

[54] PREPARATION OF A SOLID PHASE MATRIX CONTAINING A BOUND SPECIFIC BINDING PAIR

[75] Inventors: Michael Berger, Penzberg; Arno Deger, Seeshaupt; Josef Maier, Weilheim, all of Fed. Rep. of Germany

[73] Assignee: Boehringer Mannheim GmbH, Mannheim, Fed. Rep. of Germany

[21] Appl. No.: 814,310

[22] Filed: Dec. 23, 1991

Related U.S. Application Data

[63] Continuation of Ser. No. 435,427, Oct. 30, 1989, abandoned.

[30] Foreign Application Priority Data

Feb. 29, 1988 [DE] Fed. Rep. of Germany ....... 3806431

[51] Int. Cl.$^5$ .................. G01N 33/552; G01N 33/53; C12N 11/14; C12N 11/02
[52] U.S. Cl. .................................... 436/527; 435/7.1; 435/7.92; 435/7.93; 435/7.94; 435/176; 435/177; 435/178; 435/180; 435/181; 436/524; 436/528; 436/529; 436/531; 436/532; 530/811; 530/812; 530/813; 530/815; 530/816
[58] Field of Search ............. 435/7.1, 7.92, 7.93, 435/7.94, 176, 177, 178, 180, 181; 436/524, 527, 528, 529, 531, 532; 530/811, 812, 813, 815, 816

[56] References Cited

U.S. PATENT DOCUMENTS

| | | | |
|---|---|---|---|
| 4,282,287 | 8/1981 | Giese | 428/407 |
| 4,778,751 | 10/1988 | El Shami | 435/7 |
| 4,820,644 | 4/1989 | Schäfer | 436/518 |
| 5,061,640 | 10/1991 | Tischer et al. | 436/527 |

FOREIGN PATENT DOCUMENTS

| | | |
|---|---|---|
| 16552 | 10/1980 | European Pat. Off. |
| 122209 | 10/1984 | European Pat. Off. |
| 269092 | 6/1988 | European Pat. Off. |
| 8704794 | 8/1987 | PCT Int'l Appl. |
| 2103791 | 2/1983 | United Kingdom |

*Primary Examiner*—David M. Naff
*Attorney, Agent, or Firm*—Felfe & Lynch

[57] ABSTRACT

A specific binding pair is bound to an insoluble carrier for use in determining an analyte such as in an immunoassay. The carrier is coated with a first polymer containing a protein polymer having a molecular weight of at least about 20,000 and molecules of a first member of a specific binding pair. A second polymer containing a second member of the specific binding pair is bound to the first member on the carrier by binding of the first and second members of the specific binding pair. The first polymer is preferably more hydrophobic than the second polymer. The protein polymer can be prepared by cross-linking hydrophobic protein molecules of 10,000 to 700,000 molecular weight with a bifunctional or polyfunctional compound to obtain a protein polymer of 200,000 to 20,000,000 molecular weight. The second polymer can be the second member of the specific binding pair or the second member cross-linked with a linker or the second member cross-linked to a hydrophobic protein.

13 Claims, 3 Drawing Sheets

PREPARATION OF A SOLID PHASE MATRIX CONTAINING A BOUND SPECIFIC BINDING PAIR

This application is a continuation of application Ser. No. 435,427, filed Oct. 30, 1989, now abandoned.

The invention concerns a process for the production of a specifically bindable substance bound to an insoluble carrier material, useful in heterogeneous immunoassays.

In order to determine a specifically bindable substance, one frequently uses immunoassays. One of the partners of a pair of substances specifically bindable with one another is reacted with the receptor specific for it, which is labelled in per se known manner. The conjugate of these two substances can then still react with a receptor which is specific for the conjugate or for one or the two parts of the conjugate. There are many variations for these immunological processes. It is advantageous when one of the receptors is present bound to a solid phase. This simplifies the separation of bound and non-bound reaction partners. For the determination of the specifically bindable substance, the amount of labelled reaction partner bound to the solid phase or of labelled reaction partner present in the solution is then measured and placed in relationship to the amount of reaction partner to be determined in per se known way.

The solid phase is usually synthetic resin test tubes or microtitre plates on the inner surface of which is fixed the reaction partner, or spheres on the outer surface of which is fixed the reaction partner. These synthetic resin test tubes, microtitre plates or spheres usually consist of a relatively inert synthetic resin material so that the binding of the reaction partner causes difficulties. Furthermore, the binding of the specific reaction partner to the particular surface must take place so that the specific reaction partner does not lose its ability to bind the substance for which it is specific. For this reason, the binding of the reaction partner to the solid phase usually takes place adsorptively. It has, therefore, already been suggested to bring about the fixing of the reaction partner to the solid phase via a coupling agent which brings about the binding. One must take care in this case that the binding of the reaction partner to the coupling agent does not destroy the specifically reacting region of the molecule or that the reaction partner is so bound that its reactive position faces away from the solid phase towards the binding partner. Furthermore, it is suggested in DE-OS 25 33 701, that in order to achieve a better binding, to cross-link the individual immunologically effective proteins and then to adsorb these on polystyrene spheres. This reference suggests simultaneously cross-linking an inert protein to the protein with immunological properties so that a cross-linked product of inert and active protein results. This is adsorbed on polystyrene spheres. However, depending upon the selected reaction conditions, this type of cross-linking can lead to differing, non-reproduceable cross-linking with varying proportions of non-cross-linked, and unsolubilized protein. Due to the differing degree of cross-linking, products with differing binding properties also result. A similar process is described in EU-A-122 209 and also displays the same disadvantages. Thus, all these known process still do not satisfy and, still do not least to optimum adhesion of the specifically bindable substance As a result, these are of little suitability for the reproducable production of coated solid phases.

Further, another problem results from the fact that the antibody bound to the solid phase must, as a rule, be different for various tests. Therefore, for each test, a specifically coated solid phase must be available. This is very laborious. Furthermore, it is not guaranteed that each antibody immobilized in known way remains bindable. In the known processes, non-specific binding takes place and the rate at which the antibody dissolves from the matrix is very high. As a result, a large excess of antibody is necessary. Nevertheless, the number of the binding places is limited. Thus the amount of disturbances increases. This is disadvantageous since antibodies are difficult and laborious to produce.

Therefore, it is the subject of the invention to provide a process which is reproduceable, improves the adhesion of the specifically bindable substance to the solid phase and, in addition, provides a process with which a solid phase matrix can be produced which is universally useable for all immunoassays. Since, in the case of many immunological processes, one works with the addition of detergents in order to avoid turbidities and non-specific bindings, it is also the object of the invention to improve the adhesion to such an extent that, even in the presence of detergents, the bound, specifically bindable substance does not dissolve off.

This object is achieved by a process for the production of a specifically bindable protein containing substance bound to an insoluble carrier material, which is useful in heterogeneous immunoassays by coating a substance on an insoluble carrier material, which contains a first polymer having a molecular weight of more than 20,000, which itself contains a plurality of molecules of a first member of a binding pair $P_1$. This is cross-linked to a second polymer which comprises a plurality of molecules of a second member of a binding pair $P_2$. The cross-linking takes place between $P_1$ and $P_2$. The second polymer also comprises binding sites for a complex containing the analyte to be determined.

With this process, a solid phase matrix can be produced which is useable for all types of immunoassays, e.g. sandwich tests or competitive tests in the one step or two step process. For the sandwich test in the one step process, the polymer II of the partner $P_2$ can, for example, provide the binding position to which the complex to be determined is then immobilized. During the determination process, a sample which contains the substance to be determined is reacted with a labelled receptor, as well as an unlabelled receptor which is bindable with the polymer II. The complex formed from the substance to be determined, labelled receptor and receptor with binding position for the polymer II then because of its specific bindability to the polymer II so that, in this way, the whole complex is immobilized. After separation of the phases, the label can be measured in one of the two phases.

If the sandwich test is carried out in the two step process, a solid phase matrix can be used in which an unlabelled receptor is bound in the polymer II. The sample and the labelled receptor are then incubated in the presence of this solid phase matrix. After separation of the phases, the label bound in the solid phase can then be measured.

In the case of carrying out of a competitive test, sample and labelled probe analogue compete for an unlabelled receptor. In a variant of the one step process, one uses a polymer II to which the unlabelled receptor is bound. In another variant of the two step process, the unlabelled receptor is bound during the assay in competition with the labelled receptor so that, for this case, a polymer II is used which has binding positions for these receptors.

For the production of the solid phase matrix according to the invention, an insoluble carrier material is coated with a first polymer I, so that binding to the carrier material does not take place covalently but rather is brought about by adsorption or by exchange action. This first polymer is cross-linked with a second polymer II. For the polymer I, biological polymers are suitable which are water-soluble and have a molecular weight of more than about 20,000. Preferred for the polymer I are proteins, peptides, nucleic acid polymers, carbohydrates, as well as co-polymers of amino acids and carbohydrates. In addition polymers, such as carbohydrates in derivatized form, e.g. aminodextran and other derivatized polymers may be used. Furthermore, the polymer I has a plurality of partners $P_1$ of a specific binding pair. The partners $P_1$ can be cross-linked with the polymers or bound to them. The polymer I must have a molecular weight of more than 20,000 since, in the case of a lower molecular weight material being used, the binding to the insoluble material is, under certain circumstances, no longer guaranteed. Preferably, the molecular weight amounts to more than 45,000 and in an especially preferred embodiment to more than 200,000.

The binding of the partner $P_1$ to the polymer takes place in per se known way. Suitable coupling methods are described e.g. in Ishikawa, J. Immunoassay, 4, 209–327 (1983). There are thereby used either functional groups of the partner $P_1$, which are suitable for binding with the polymer, or, when suitable functional groups are not present, these are introduced into the $P_1$ molecule. Thus, for example, when biotin is $P_1$, the N-hydroxysuccinimidyl derivative can be bound by reaction with, amino groups present in the polymer. Other suitable materials achieving this aim are known to the expert and do not need to be explained here.

The ratio of the partner $P_1$ to the polymer used for the polymer I is not critical and can vary. It has been shown that it is advantageous to use 1 to 200 moles of partner $P_1$ per polymer. The amount of $P_1$ used depends upon both the intended use of the carrier and polymer used. Since the polymer I is, as a whole, to be relatively hydrophobic in order to bring about adsorptive binding, when $P_1$ is hydrophilic, the proportion of $P_1$ should decrease when the molecular weight of the polymer decreases. This is the case, e.g., with biotin.

Suitable binding partners which can be used as $P_1$ and $P_2$, as well as in the binding between the polymer II and the complex to be detected immunologically are e.g. biotin-avidin, biotin-streptavidin, antigen-antibody, hapten-antibody, protein A-immune-$\gamma$-globulin and protein G-immune-$\gamma$-globulin. As antigen or hapten are also understood conjugates of proteins with antigen or hapten or fragments thereof. The antigen can itself also be an antibody, its Fab, Fab' or (Fab')$_2$ fragment. By antibodies are to be understood monoclonal and polyclonal complete antibodies and antibody fragments. If, as $P_1$ or $P_2$, protein A or protein G is used, then, in the immunoassay, only one receptor, which is to be bound to the solid phase, should be a complete antibody, whereas as the labelled receptor there should be used a Fab or F(ab')$_2$ fragment in order not to bring about a non-specific binding of the labelled receptor with the solid phase which would lead to a falsification of the result.

For the production of the polymer I, a protein Which is more hydrophobic than the partners $P_1$ and $P_2$ is preferred. Especially suitable are soluble proteins with a molecular weight of above about 200,000 to about 20,000,000, which have possibly been obtained from proteins with a molecular weight of 10,000 to 700,000. These are conjugated with partners $P_1$ of a specific binding pair.

Molecular weight and hydrophobicity are determined by methods known to the expert. For the comparison of the hydrophobicity between soluble protein and specific bindable substances, there are suitable, for example, the following methods:

the fluorescence extinction after binding to coloured material (Biochem. Biophys. Acta 624, (1980), 13–20), the elution behaviour using hydrophobic chromatography (Biochem. Biophys. Acta, 576 (1979), 269–279), the surface tension (Biochem. Biophys. Acta, 670 (1981), 64–73), the retention time using hydrophobic interaction chromatography (HIC)(Angew. Chemi 98 (1986) 530–548, J. Chromat. 296 (1984) 107–114, Anal. Biochem. 137, (1984) 464–472).

A comparison of the hydrophobicity of substances suitable according to the invention is found in Sep. Sci. Technol. 14, 305–317 (1979). According to this reference the hydrophobicity increases in the following series:

$\alpha_2$-macroglobulin (M.W. 820,000)
bovine serum albumin/human serum albumin (M.W. 70,000)
egg albumin
$\alpha_2$HS-glycoprotein (M.W. 49,000)
$\beta_{1c}/\beta_{1A}$-globulin
immunoglobulin (M.W. 150,000)
transferrin (M.W. 90,000)

Thus, if an immunoglobulin is used as specific bindable substance, human serum albumin or $\alpha_2$HS-glycoprotein are not suitable as soluble proteins without further pretreatment.

Both proteins must here be subjected not only to hydrophobing but also to an increase of the molecular weight. In the case of transferring, in this case cross-linking suffices, in the case of $E_2$-macroglobulin hydrophobing is sufficient.

Proteins which are suitable for the coupling with immunoglobulin as specific bindable substance without pretreatment are, for example, $\beta$-lipoproteins (M.W. about 3.2 million) or $\alpha_2$-lipoproteins (M.W. about 5 to 20 million). The proteins can be made hydrophobic, for example, by the use of heat, treating with acids, denaturing agents and/or chaotropic ions and/or by chemical coupling with a hydrophobic compound.

The increases of the molecular weight can take place, for example, by the use of heat, treatment with acids, denaturing agents and/or chaotropic ions and/or by cross-linking with a bi- or polyfunctional compound.

A protein which is not sufficiently hydrophobic or the molecular weight of which is not sufficiently high is treated until a protein polymer is obtained with a molecular weight of 20,000, preferably 45,000 and especially more than 200,000. Especially preferred is a protein polymer with a molecular weight of 500,000 to 20,000,000.

If the protein is to be cross-linked, hydrophobing can take place before, during or after the cross-linking. However, the hydrophobing cannot be carried out in the presence of a specifically bindable substance when the specifically bindable substance is a protein and loses its biological activity due to the hydrophobing.

In order to render the proteins hydrophobic using heat, a temperature of from 40° C. to 95° C. is used in a period of time of 1 min. to 10 hours, as described, for example, in Biochem. Biophys. Acta 624 (1980) 13–20.

When treating with acids, acetic acid, propionic acid, lactic acid or hydrochloric acid are all suitable. Usual concentrations are 1 to 100 mmol/l, treating the protein for a period of 10 min to 16 hours.

When treating with chaotropic ions, thiocyanates, iodides, fluorides, bromides, perchlorates and sulphates are suitable. As denaturing agents, guanidine hydrochloride or urea are suitable. Concentrations of 10 mmol/l to 6 mol/l are here usually employed.

In order to derivatize the polymer I with hydrophobic compounds, soluble fatty acids, lipoids in low or high molecular form, as well as synthetic polymers, such as polypropylene glycol or soluble co-polymers of polystyrene are preferred. The derivitization takes place according to methods familiar to the expert.

The cross-linking is carried out with bi- or polyfunctional compounds. These are compounds which carry at least two functional groups which can be the same or different and which can react with functional groups of the compounds forming the polymer I, e.g. of proteins. Compounds are preferably used which consist of an alkyl chain on the ends of which are present succinimide, maleinimide and/or aldehyde groups.

The cross-linking is then carried out with the bi- or polyfunctional compound in per se known way.

Proteins with a molecular weight of 10,000 to 700,000 are preferably used for the hydrophobing and/or cross-linking. Bovine serum albumin, lipase or immune-γ-globulin are especially preferred.

The polymer I produced in this way is then bound to an insoluble carrier material. The binding thereby takes place via the polymer and is, as a rule, adsorptive. As carrier materials those known in the art may be used, such as Luran, glass, titanium dioxide, polystyrene, γ-activated polystyrene, polystyrene-acrylonitrile co-polymer, paper and/or polyolefin. Before further work up, the carrier material can be physically or chemically pre-treated. Thus, for example, a synthetic resin surface can be pre-swollen or activated in another per se known way. As a rule, the carrier material is present in the form of small tubes, microtitre plates or spheres. However, other shapes are also possible.

The insoluble carrier material can also be an already coated material. Small tubes pre-coated with polystreptavidin or small tubes pre-coated with polymerized antigen are suitable. In this case, the insoluble carrier material provides binding positions for the polymer I so that the binding of the polymer I takes place not only adsorptively. In this way, very strong binding is obtained. In the case of the adsorptive binding, the polymer I is not very strongly bound. However, this suffices for most purposes of use since even in the case of dissolving off of some $P_1$, the wall adhesion is stabilized by the cross-linking with the polymer II. For special purposes, stronger binding may be desired. For this case, a pre-coated material can be used as insoluble carrier material.

The polymer I is cross-linked with a second polymer II which displays a plurality of partners $P_2$. The polymer II can consist either only of $P_2$ or of a mixture of $P_2$ and other components. The polymer II has not only binding positions for $P_1$ which are provided by $P_2$ but, in addition, also binding positions for a complex to be detected immunologically which, in the following, is to be designated as receptor. The term "receptors" as used herein refers to specifically bindable substances, especially either specifically bindable complete antibodies, which can be polyclonal or monoclonal, their antibody fragments or conjugates of antibodies or antibody fragments with haptens or antigens, as well as haptens or antigens or binding proteins (such as e.g. thyroxine-binding globulin). The binding positions for the receptor can either provided by $P_2$ or from another component of the polymer II.

The individual partners $P_2$ can be joined with one another via homo- or heterobi- or polyvalent compounds (linkers). The cross-linking is then preferably carried out with bivalent linkers since this makes possible an easier control of the degree of polymerization. However, polyvalent linkers are also suitable. As linkers, there can be used those compounds which display reactive groups which, in aqueous solution, are able to react with the functional groups of the specific bindable partner with formation of a covalent bond. A large number of bifunctional or polyfunctional linkers suitable herefor is known to the expert. Typical examples of homo- or heterobifunctional and trifunctional linkers well suited in cope of the invention are set out in the following Table 1.

TABLE 1

| short designation | chemical designation |
| --- | --- |
| SPDP | N-succinimidyl 3-(2-pyridyldithio)-propionate |
| EADB | ethyl 4-azidophenyl-1,4-dithiobutyrimidate.HCl |
| FNPA | 4-fluoro-3-nitrophenylazide |
| HSAB | N-hydroxysuccinimidyl-4-azisobenzoate |
| MABI | methyl 4-azidobenzoimidate.HCl |
| MBS | m-maleimidobenzoyl-N-hydroxysuccinimide ester |
| NHS-ASA | N-hydroxysuccinimidyl-4-azidosalicylic acid |
| MHS | maleimidohexanoyl-N-hydroxysuccinimide ester |
| PNP-DTP | p-nitrophenyl-2-diazo-3,3,3-trifluoro-propionate |
| SADP | N-succinimidyl-(4-azidophenyl)-1,3'-dithiopropionate |
| SAND | sulphosuccinimidyl-2-(m-azido-o-nitro-benzamido)-ethyl-1,3'-dithiopropionate |
| SANPAH | N-succinimidyl-6-(4'-azido-2'-nitrophenyl-amino)-hexanoate |
| SASD | sulphosuccinimdyl 2-(p-azidosalicylamido)-ethyl-1,3'-dithiopropionate |
| SIAB | N-succinimidyl-(4-iodoacetyl)-aminobenzoate |
| SMCC | succinimidyl-4-(N-maleinimidoethyl)-cyclohexane-1-carboxylate |
| SMPB | succinimidyl-4-(p-maleimidophenyl) butyrate |
| DSS | disuccinimidyl suberate |
| DMS | dimethyl suberimidate |
| Traut's reagent | 2-iminothiolane |
| | 2,4,6-trichloro-s-triazine |
| SAMBA | S'-acetylmercaptosuccinic acid anhydride |

In order to carry out the cross-linking, a solution of the partner $P_2$ can be mixed with the linker molecules under conditions which lead directly to the cross-linking. The extent of the cross-linking is, in this case, controlled by the amount of added linker.

In a further preferred embodiment, the binding partner $P_2$ is cross-linked with suitable bindable components which are inert with regard to $P_1$ and the complex to be determined. Suitable herefor is, for example, a soluble protein, such as was defined above, especially bovine serum albumin or human serum albumin.

The heterogenous cross-linking can, for example, so take place that not only the protein material used as "inert component" but also the specific bindable partner $P_2$ are provided with an activated bindable group and subsequently reacted. In this way, one obtains a cross-linked polymer which contains a sufficient amount of bindable partner $P_2$. Of course, the binding of the partner $P_2$ to the protein must take place so that neither the specific bindability with the partner $P_2$ is impaired nor is the specific binding position for the complex to be determined blocked.

In a further preferred embodiment of the process according to the invention, the binding partner $P_2$ is cross-linked with other components which display specific binding positions for the receptor. This embodiment is then preferred when $P_2$ has only one specific binding position for the binding with $P_1$. The other component then provides the binding position for the receptor to be bound. As other components, substances which have specific binding positions, especially partners of a specific binding pair as were defined above are suitable.

In order to coat the soluble carrier material with the polymers I and II, various ways are available. In a first embodiment, the insoluble carrier material is first coated with the polymer I i.e. the carrier is incubated with a solution which contains polymer I. When the polymer I is bound, a solution which contains polymer II is subsequently added thereto, whereby, due to the specific binding of $P_1$ and $P_2$, the cross-linking of the two polymers takes place.

In a further embodiment of the process according to the invention, the insoluble carrier material is incubated with a solution which contains not only polymer I but also polymer II and, additionally, an inhibitor which inhibits the binding of $P_1$ to $P_2$. An inhibitor is used with inhibitory effect that can be reversed and which loses its inhibiting action by simple removal or chemical change. In the presence of the inhibitor, the partners $P_1$ and $P_2$ can be homogeneously distributed and, since the binding taking place very slowly, one obtains a completely uniform coating of the carrier material with the particular desired binding-active substance which, even in large-scale use, leads to fully uniform and reproduceable results. This embodiment is suitable when, as binding partner $P_1-P_2$, are antigen or hapten-antibody or biotin-streptavidin or avidin. Within the scope of this invention, "inhibitors" includes those substances which are used as desorption agents in chromosorptive purification. These substances inhibit binding of $P_1$ and $P_2$. Especially preferred herefor are acids, bases or chaotropic ions of the Hofmeister series (lyotropic series), such as are described, for example, in "Structure and Stability of Biological Macromolecules", 1969, Marcel Dekker Inc., New York, page 427, as well as certain organic compounds or solvents, such as acetonitrile, urea or glycerol. Volatile and non-volatile acids are suitable. Volatile acids can easily be removed, e.g. by heating, vacuum and the like. When non-volatile acids are used, an analogous effect can be achieved by use of a salt of a volatile acid which is decomposed by the nonvolative acid with liberation of the volatile acid, or by rebuffering. Preferred examples for volatile acids are acetic acid, propionic acid and hydrochloric acid.

Similarly, volatile and non-volatile bases can be used, such as ammonia and t-phosphate. Furthermore, organic compounds are suitable as inhibitors which can reversably influence not only the protein but also the water structure and are described, for example, in "J. F. Brandts, Conformational Transitions of Proteins in Water", contained in "Structure and Stability of Biological Macromolecules, 1969, Marcel Dekker Inc. New York, page 213-290. Glycerol and urea are especially preferred.

As inhibitors chaotropic ions, such as thiocyanates and iodides can be used. Also suitable are fluoride, bromides, perchlorates, guanidine and sulphates. Their removal can take place by extraction e.g. with organic solvents or mixtures of organic solvents or mixtures of organic solvents and water, for example water/alcohol mixtures, possibly with the addition of ionophores and the like. As a rule, a change of the ionic strength suffices in order to achieve the desired effect but a complete removal of the inhibitor can also take place. An addition of complex formers, such as EDTA, can be used for the removal of inhibiting metal salts, such as $MgCl_2$.

If, for polymers I and II, biotin and streptavidin or avidin are used as binding pair, then an acid is especially preferred as inhibitor. The strong binding of these two partners can be inhibited by lowering of the pH to values in the region 4 and below. For this purpose, a volatile acid is preferred so that the binding action is restored by liberation of the volatile acid.

The two specific binding partners $P_1$ and $P_2$ and possibly the other components are preferably used in such a ratio that $P_2$ and possibly the other components are present for the binding of the receptor in large excess in comparison with their binding partners. In this way, very many binding positions are provided for the complex to be immobilized. When a partner of the specific binding pair used is present as native substance in the sample liquid to be analysed, it is especially preferred to make available a high binding capacity for this substance in order to exclude disturbance. Thus, when biotin and streptavidin or avidin are used as specific binding pair, it is preferred to make available a very high binding capacity for the biotin. Biotin is present in body fluids and can falsify analysis values or determinations when a biotin conjugate is used. This is especially true when the subject is taking biotin, and serum is being analyzed. For this case, it is especially preferred to produce a solid phase matrix with a very high binding capacity for biotin. This takes place with the process according to the invention by providing a binding capacity of 200 ng./ml. and more for biotin.

The solid phase matrix produced according to the invention is used in determinations according to the immunoassay principle. It is suitable not only for the variants of the sandwich test but also for the variants of the competitive test. For example, the sample which contains the substance to be determined can be reacted with a receptor which carries a label and at least one further receptor to which is bound a substance specifically bindable with the polymer of the specific binding partner $P_2$. The complex to be determined, preferably one of the bound receptors, displays a position which is bindable with the polymer. This binding position can be identical with that of $P_1$ or a different one. This reaction can take place in a test tube coated with the matrix according to the invention or a correspondingly coated microtitre plate. However, it is also possible to add the solid phase matrix, e.g. in the form of spheres, after the incubation. In the case of contact with the solid phase matrix, the complex of substance to be determined, labelled receptor and receptor conjugated with specific binding substance then binds to the polymer which again is bound to the carrier via $P_1$ and the protein. In this way, the complex to be determined can be immobilized.

A further object of the invention is a solid phase matrix which is characterized in that it consists of an insoluble carrier material to which is bound a polymer I, which has a plurality of partner $P_1$ of a specific binding pair which is cross-linked with a polymer II of a plurality of the other partner $P_2$ of the specific binding pair, whereby the polymer II has binding positions not only for $P_1$ but also for a complex to be detected immunologically.

Especially suitable for the carrying out of immunoassays is a solid phase matrix in which the protein is a conjugate of a soluble protein with a molecular weight of 200,000 to 20,000,000 and a plurality of biotin, avidin or streptavidin molecules. In an especially preferred embodiment, a solid phase matrix is used in which the polymer II consists of biotin, avidin or streptavidin molecules. The polymer II is preferably formed from biotin, avidin or streptavidin molecules, on the one hand, and a hydrophobed protein, on the other hand.

According to the invention, a universal matrix is made available, as well as process for its production, which can be used in all immunoassays.

The solid phase matrix is independent of the nature of the receptors used. Furthermore, it is characterized by high stability.

BRIEF DESCRIPTION OF THE FIGURES

FIG. 1 shows two embodiments of the solid phase matrix according to the invention.
  a) shows one embodiment of the solid phase matrix according to the invention. A conjugate of a protein 3 with a partner of a specific binding pair $P_1$ 5 is adsorbed on a solid phase 1. A polymer 7 is bound to 5 which consists of the other partner $P_2$ of the specific binding pair. The polymer consists of homogeneously cross-linked identical molecules. In carrying out an immunoassay, antibodies 9 bind to this polymer which are conjugated with $P_1$.
  b) shows a further embodiment of the solid phase matrix according to the invention. Here, a conjugate of a protein 3 and a partner of a specific binding pair $P_1$ 5 is adsorbed on a solid phase 1. A polymer 7, is bound on 5. This polymer consists of the other partner of the specific binding pair $P_2$, as well as a receptor R. In the carrying out of an immunoassay, antibodies 9 which are conjugated with a substance bindable with the receptor R bind to this polymer.

Figure 3:
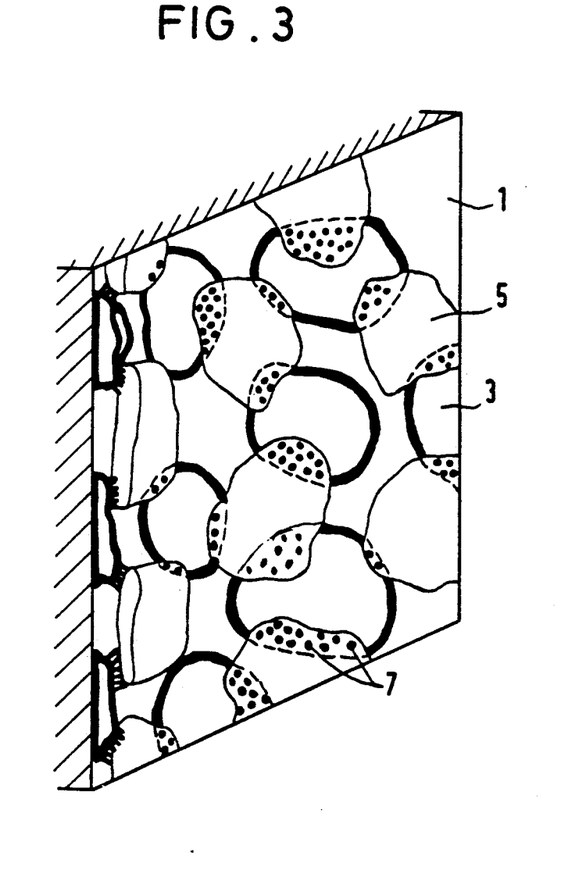
FIG. 3 shows an embodiment of the solid phase matrix according to the invention.

In this embodiment, a first component 13 which has a plurality of partners of a specific binding pair is adsorptively bound to a carrier material 11. A second component 15, which contains a plurality of the other partner of the specific binding system, is bound via the specific binding 17 of the two partners to the first component 13, forming cross-linked polymers of considerable size on the carrier material 11.

DETAILED DESCRIPTION OF PREFERRED EMBODIMENTS

Example 1

1a) Preparation of Thermo-bovine Serum Albumin-biotin 1 g. Bovine serum albumin (BSA) is dissolved in 50 ml. 50 mM potassium phosphate (pH 7.8). While stirring, 1.9 ml. D-biotinyl-ε-aminocaproic acid N-hydroxysuccinimide ester (NHS-X-biotin, Boehringer Mannheim GmbH) in dimethyl sulphoxide (DMSO)(20 mg./ml.) are added dropwise thereto. Subsequently, it is incubated for 3 hours at 25° C. After the reaction, it is dialysed overnight at 4° C. against a 50 fold volume of 20 mM potassium phosphate (pH 7.0). The retentate is mixed with the same volume of 20 mM potassium phosphate/200 mM sodium chloride (pH 7.0), heated to 70° C. and incubated at this temperature for 4 hours with careful stirring. Subsequently, the solution is cooled to room temperature and filtered. The filtrate is dialysed overnight at 4° C. against a 50 fold volume of 2 mM potassium phosphate (pH 7.0) and subsequently lyophilized. The product obtained is adsorbed on the solid phase and represents the partner $P_1$ bound to the soluble protein.

1b) Activation of Streptavidin with Maleimidiohexanoyl-N-hydroxysuccinimide Ester 30 mg. Streptavidin are dissolved in 3 ml. 30 mM potassium phosphate/100 mM sodium chloride (pH 7.1) and heated to 25° C. While stirring, 0.15 ml. maleinimido-hexanoyl-N-hydroxysuccinimide ester (MHS)(Boehringer Mannheim GmbH) in DMSO (10 mg/ml.) are added dropwise thereto. After a reaction time of 1 hour at 25° C., the solution is cooled in an icebath. Subsequently, it is dialysed at 4° C. twice against 1 l. 50 mM potassium phosphate/100 mM sodium chloride (pH 5.0).

1c) Activation of Streptavidin with S-acetylmercaptosuccinic Acid Anhydride 30 mg. Streptavidin are dissolved in 3 ml. 100 mM potassium phosphate (pH 7.8) and heated to 25° C. While stirring, 0.175 ml. S-acetylmercaptosuccinic acid anhydride (SAMBA) in DMSO (10 mg/ml.) are added dropwise thereto. After a reaction time of 3 hours at 25° C., it is dialysed at 4° C. twice against 1 l. 50 mM potassium phosphate/2 mM EDTA (pH 6.5).

1d) Homogeneous Cross-linking of Streptavidin 3 ml. of a solution of activated SAMBA-streptavidin (10 mg/ml.) (preparation according to Example 1c) are heated to 25° C. and mixed with 50 μl. 1M hydroxylamine (pH 6.5). After 30 minutes at 25° C., it is diluted by the addition of 15 ml. 50 mM potassium phosphate/100 mM sodium Chloride/1 mM EDTA (pH 6.5). The homogeneous cross-linking of the streptavidin is started by the addition of 3 ml. activated MHS-streptavidin (10 mg./ml.) (preparation according to Example 1b). After a reaction time of 2 hours at 25° C. with careful stirring, the reaction is ended by the addition of 0.2 ml. 100 mM cysteine/HCl. After an incubation time of 30 minutes at 25° C., the pH value of the solution is adjusted to 7.5 with 1M dipotassium hydrogen phosphate. After the addition of 0.2 ml. 500 mM iodoacetamide, it is incubated a further hour at 25° C. Subsequently, it is dialysed at 4° C. twice against 3 l. 50 mM potassium phosphate/100 mM sodium chloride (pH 7.5). After the dialysis, the conjugate is concentrated in an ultra-filtration cell.

The homogeneous cross-linked streptavidin can be used either directly or after gel filtration (Superose 6 prep. grade, Pharmacia Uppsala) and renewed concentration for the adsorption on the solid phase. In the matrix according to the invention, it represents polymer II.

Example 2

Heterogeneously cross-linked streptavidin is prepared which is used as polymer II in the matrix according to the invention.

a) Preparation of Activated SAMBA-thermo-BSA

The preparation of thermo-BSA takes place as described under Example 1a) with the exception that, the biotinylation is omitted.

68 mg. Thermo-BSA are dissolved in 2 ml. 0.1M potassium phosphate (pH 7.8) and slowly mixed with 0.38 ml. SAMBA (10 mg./ml. in DMSO). After a reaction time of 3.5 hours at 25° C., it is dialysed at 4° C. twice against 1 l. 50 mM potassium phosphate (pH 6.5).

b) Preparation of the Thermo-BSA-streptavidin Conjugate

The heterogeneous cross-linking of streptavidin with thermo-BSA takes place analogously to the homogeneous cross-linking described under Example 1d). 60 mg. activated MHS-streptavidin (preparation according to Example 1b)) are reacted with 68 mg. activated SAMBA-thermo-BSA (v. supra). The reaction product is purified by gel filtration (Superose 6 prep. grade) and concentrated n an ultrafiltration cell. The product obtained is subsequently lyophilized. The product can be used as polymer II.

Example 3

Loading of Luran (polystyrene-acrylonitrile co-polymer) or of γ-irradiated Polystyrene Test Tubes The products obtained according to Example 1 and Example 2 are dissolved in 50 mM potassium phosphate (pH 7.4) to a concentration of 10 μg./ml. Then, each test tube to be loaded was filled 1.5 ml. of a solution of the thermo-BSA-biotin conjugate prepared according to Example 1a) and first loaded for 3 to 5 hours. Subsequently, after complete removal of the solution by aspiration, the test tubes are incubated with 1.5 ml. of a solution of homogeneously cross-linked streptavidin according to Example 1 or of heterogeneously cross-linked streptavidin according to Example 2, overnight at room temperature. Thereafter, the test tubes are completely emptied and used for the corresponding test.

For comparison, test tubes are loaded only with streptavidin cross-linked according to Example 1 or a conjugate of (non-thermally aggregated) BSA and streptavidin (preparation analogous to Example 2 from activated SAMBA-BSA and activated MHS-streptavidin), without pre-loading with biotinylated polymer I.

Example 4

The binding capacity of the test tubes produced according to Example 3 is determined.

The test tubes loaded with the different streptavidin polymers according to the invention, as well as the comparison test tubes, are incubated for 45 minutes at room temperature with 1 ml. of a solution of biotinylated peroxidase from horseradish (biotin-POD, Sigma) (10 mU/ml. in 50 mM potassium phosphate (0.5% bovine serum mU/ml. in 50 mM potassium phosphate (0.5% bovine serum albumin (pH 7.4). The test tubes are then emptied and washed twice with bidistilled water. Subsequently, the detection reaction takes place with the help of ABTS® (ammonium salt of 2,2'-azino-di-(3-ethylbenzothiazoline-6-sulphonic acid) for 30 minutes at room temperature. The measurement takes place photometrically at 405 nm. The binding capacity (bica) is determined via a displacement curve. For this purpose, increasing concentrations (0 to 15 or 0 to 200 ng./ml.) of D-biotin (Sigma) are added to the biotin-POD solution. The binding capacity is then calculated from the curves obtained by plotting the individual values from the semi-maximum extinction.

Example 5

The stability of the surface adhesion of the matrix coated with protein and biotin and, in each case, a streptavidin polymer is tested by incubation of the loaded test tubes with 1.5 ml. of a detergent-containing dissolving-off buffer (0.2% Tween 20 in 50 mM potassium phosphate (pH 7.0)). After an incubation time of one hour at room temperature, in order to determine the dissolved-off amount of conjugate, in each case 1 ml. is transferred from the test tubes into a test tube coated with thermo-BSA-biotin (produced according to Example 1a). In parallel, for the determination of a calibration curve, thermo-BSA-biotin test tubes were mixed with 1 ml. dissolving-off buffer which contains increasing concentration of streptavidin. After an incubation time of one hour at room temperature, the test tubes are completely emptied and mixed with 1 ml. of a biotin-POD solution (100 mU/ml. in 50 mM potassium phosphate (pH 7.0)). After a further incubation of 30 minutes at room temperature, the tubes are emptied and subsequently washed three times with bidistilled water. The amount of bound biotin-POD is proportional to the amount of conjugate dissolved off from the test tube wall and is determined photometrically by the substrate reaction with ABTS (incubation one our at room temperature). On the basis of the calibration curve, the amount o dissolved-off conjugate and designated as dissolved-off biotin binding capacity is quantified.

Table 2 shows, for various loaded Luran and γ-irradiated polystyrene test tubes (PS), the biotin binding capacity determined according to Example 4 and the desorption of the conjugate determined according to Example 5. The biotin binding capacity (and thus the binding capacity for biotinylated antibody) of the specific binding partner directly homogeneous cross-linked on the solid phase (comparison)(in the Example polystreptavidin) is clearly greater than that of the specific binding partner bound heterogeneously cross-linked directly on the solid phase (comparison)(in the Example BSA-streptavidin, preparation analogous to Example 2) from activated SAMBA-BSA and activated MHS-streptavidin). As the dissolving-off data show, the cross-linked specific binding partner $P_2$ can only be applied with high binding capacity and the desired firm wall adhesion when loading with pre-cross-linked protein, which contains the specific binding partner $P_1$, i.e. biotin and loaded previously, covalently bound, is reacted in situ. The influence of the binding capacities and solid phase dissolvings-off of the various conjugates on the sensitivity of a function test carried out with the use of detergents is described in more detail in Example 6.

| coating | BSA-SA (comparison) | pSA (comparison) | pSA (comparison) | T-BSA-biotin[1] + T-BSA-SA[2] (invention) | T-BSA-biotin[1] + pSA[2] (invention) |
|---|---|---|---|---|---|
| test tube material | γ-PS | γ-PS | Luran | Luran | Luran |
| loading concentration (μg./ml) | 10 | 10 | 10 | 10[1]/8[2] | 10[1]/8[2] |
| biotin-bica (ng) | 7.5 | 58 | 60 | 15 | 120 |
| desorption (Bi-bica (ng) | 0.017 | 0.267 | 9.3 | 0.005 | 0.015 |
| % Bi-bica loss | 0.3 | 0.5 | 15.5 | 0.03 | 0.01 |

Example 6

The test tubes obtained according to Example 3 are used in a TSH test.

Reagents

Reagent 1 (Antibody Incubation Solution)

16 mmol/l. phosphate buffer pH 6.9

1.5 μg.ml. biotinylated monoclonal antibody against TSH (ECACC 87122201)(the biotinylation took place according to JACS 100 (1978), 3585–3590 with biotin by reaction with N-hydroxy-succinimide-biotin in the ratio of 10:1).

Reagent 2 (Antibody-POD Conjugate Solution)

36 mMol/l. phosphate buffer pH 6.9

2.0 U/ml. conjugate of POD and monoclonal antibodies against TSH (ECACC 87122202)

Reagent 3 (Substrate Chromogen Solution) 100 mMol/l. phosphate-citrate buffer pH 4.4

3.2 mMol/l. sodium perborate 1.9 mMol/l ABTS (2,2'-azino-di-[3-ethylbenzthiazoline-sulphonic acid-(6)]-diammonium salt)

As solid phase test tubes are used which have been coated as described in Example 3 with various matrices. In these test test tubes 0.2 ml. sample (TSH standard), 0.9 ml. reagent 1 and 0.1 ml. reagent 2 are placed and incubated for two hours at room temperature. Subsequently, the test tubes are completely emptied and washed three times with water. The POD activity bound to the test tube wall is then determined, after addition of 1 ml. of reagent 3 and incubation for one hour, by measurement of the extinction at 405 nm. The intensity of the colour reaction is proportional to the TSH concentration of the standard. The results are shown in FIG. 2.

Figure 1A:
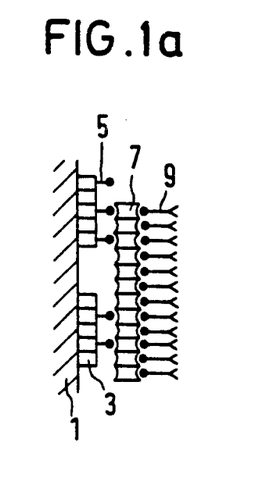
Figure 1B:
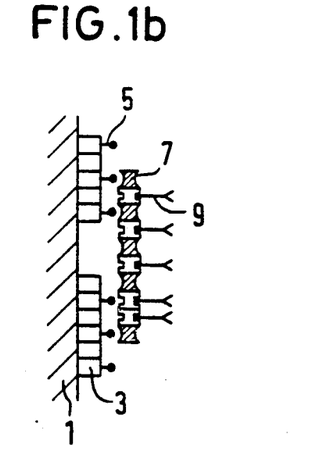
Figure 2:
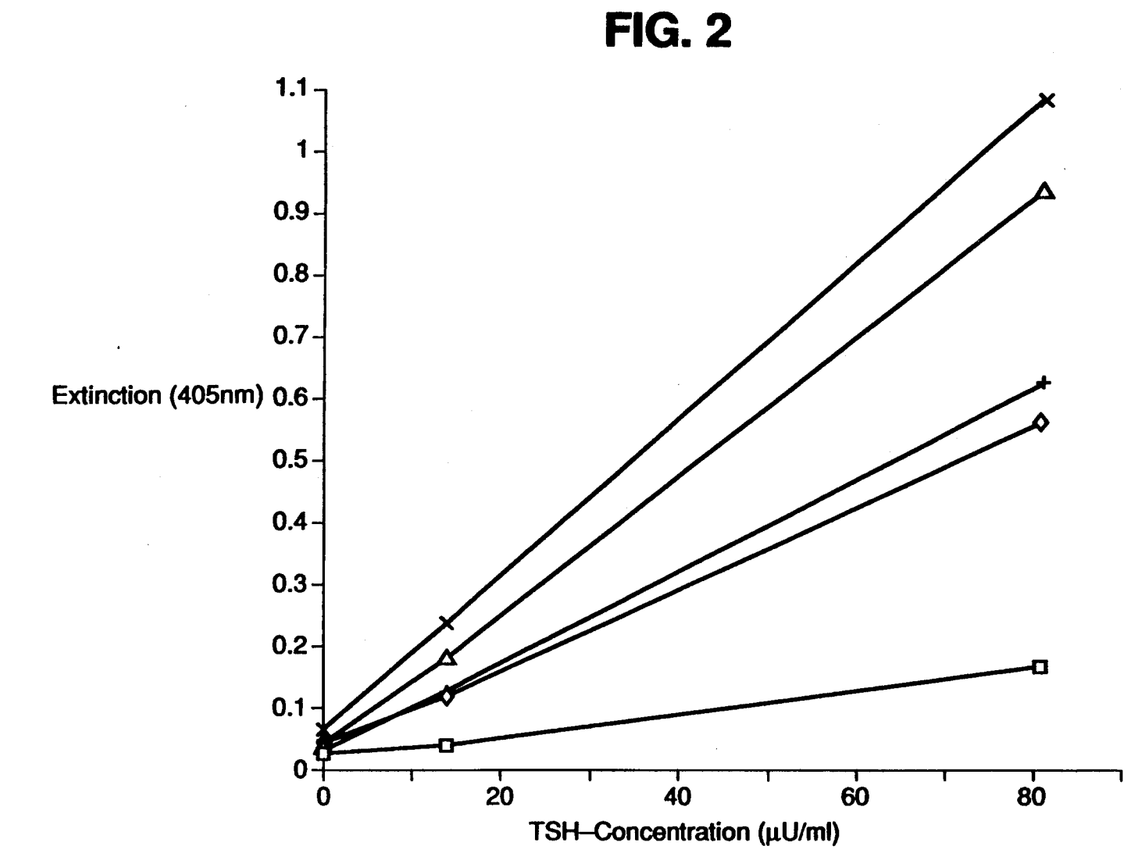
FIG. 2 shows a diagram in which calibration curves for various coated test tubes have been plotted.
The individual curves were obtained with the following test tubes:
X: Luran test tubes coated with a two-component matrix consisting of thermo-BSA-biotin and homogeneously cross-linked streptavidin.
triangle: Luran test tubes coated with a two-component matrix consisting of thermo-BSA-biotin and thermo-BSA-streptavidin.
+: polystyrene test tubes, gamma-irradiated and coated with BSA-streptavidin.
diamond: polystyrene test tubes, gamma-irradiated and coated with homogeneously cross-linked streptavidin.
square: Luran test tubes coated with homogeneously cross-linked streptavidin.

As FIG. 2 shows, the gradient of the calibration curve (and thus the sensitivity of the test) increases clearly in the case of use of detergent-containing incubation buffer from test tubes which are loaded with a one-component matrix as compared to test tubes which are loaded with the two-component matrix according to the invention. Furthermore, the greatest sensitivity is achieved by use of the two-component matrix which, as component B, contains a homogeneously cross-linked binding partner (here polymeic streptavidin).

Example 7

A matrix is produced which has thermo-BSA adsorbed thereto with streptavidin bound as the partner $P_1$. The streptavidin is then coupled to homogeneously cross-linked, biotinylated protein A as partner $P_2$.

a) Preparation of Thermo-BSA-Streptavidin

The preparation takes place as described under Example 2.

b) Preparation of Homogeneously Cross-linked, Biotinylated Protein A 50 mg. Protein A (Boehringer Mannheim GmbH) are dissolved in 5 ml. 30 mM potassium phosphate (pH 7.1) and mixed with a 10 fold molar excess of NHS-X-biotin (dissolved at 10 mg./ml. in DMSO). After an incubation time of one hour at 25° C., the reaction mixture is dialysed at 4° C. overnight against 10 l. 50 mM potassium phosphate (pH 8.0). The retentate is subsequently concentrated in an ultrafiltration cell to a concentration of 50 mg biotin-protein A/ml.

The concentrated solution of biotin-protein A is warmed with 25° C. Subsequently, with careful stirring, 50 μl of a disuccinimidyl suberate solution (DSS, firm Pierce; 7 mg/ml in dioxan) are added thereto. The cross-linking is controlled by HPLC on a TSK 3000 gel filtration column (LKB). At intervals of one hour, in each case 50 μl of the DSS solution are added thereto until the peak of the monomeric protein A has been reduced to less than 10% of its initial size. Thereafter, the further cross-linking is stopped by the addition of 50 μl 1M ethanolamine (pH 8.0). It is incubated overnight at 4° C. and subsequently dialysed twice against 2 l. 2 mM potassium phosphate (pH 7.5). The separation of the monomeric protein A takes place by gel filtration on Superose 12 prep. grade. The homogeneously cross-linked product is collected and concentrated in an ultrafiltration cell. Test tubes are then loaded With these two components according to Example 3.

Example 8

A matrix is prepared consisting of a conjugate of thermo-BSA with Fcγ fragments of the mouse as $P_1$ and a homogeneously cross-linked polyclonal anti-mouse Fcγ-antibody from sheep as $P_2$.

Preparation of Thermo-BSA-Mouse Fcγ Fragments

The Fcγ fragments are prepared by papain cleavage of immunoglobulin G of the mouse and separation of the Fab fragments by ion exchange chromatography on DE-52 cellulose according to usual processes.

Activated MHS-Fcγ fragment is prepared and analogously to the preparation of activated MHS-streptavidin (Example 1b)). Activated SAMBA-thermo-BSA is prepared as described in Example 2. The conjugation of 68 mg activated SAMBA-thermo-BSA with 10 mg activated MHS-Fcγ fragment takes place in the same way as the preparation of heterogeneously cross-linked streptavidin (Example 2). The reaction product is purified by gel filtration on Superose 6 prep. grade, concentrated in an ultrafiltration cell and is subsequently lyophilized.

b) Preparation of Homogeneously Cross-linked Anti-mouse Fcγ Antibody 50 mg Anti-mouse Fcγ antibody are dissolved in 1 ml 50 mM potassium phosphate pH 8.0 and warmed to 25° C. Analogously to the preparation of homogeneously cross-linked protein A (Example 7b), at intervals of one hour, in each case there are added 50 μl of a DSS solution (7 mg/ml in dioxan) until in the HPLC analysis on a TSK 3000 gel filtration column, the peak of the monomeric IgG has lowered to 10% of its initial size. Subsequently, as described under Example 7b), the reaction is stopped with ethanolamine and dialysed. The monomeric IgG is separated by gel filtration as described in Example 7b). The cross-linked IgG is possibly concentrated by ultrafiltration. Alternatively, the homogeneously cross-linked product can be prepared by activation of the antibody with MHS and SAMBA (preparation analogous to Examples 1b) and 1c)) and subsequent cross-linking (analogous to Example 1d).

Test tubes are loaded with these products obtained according to a) and b) according to Example 3.

Example 9

A matrix is produced consisting of a thermo-BSA-digitoxigenin conjugate as polymer I and homogeneously cross-linked anti-digoxin antibody from sheep as polymer II.

a) Preparation of Thermo-BSA-digitoxigenin

Thermo-BSA-is prepared as described in Example 1a), but biotinylation is omitted. 68 mg Thermo-BSA are dissolved in 6.8 ml. 50 mM potassium phosphate/100 mM sodium chloride (pH 8.5) and warmed to 25° C. While stirring, there are added thereto 2.86 mg digitoxigenin-3-succinimidyl-hydroxysuccinimide ester in 0.68 ml dioxan. After a reaction time of 3 hours at 25° C., this is dialysed twice against 1 l. 2 mM potassium phosphate (pH 7.2). Subsequently, the reaction product is concentrated in an ultrafiltration cell.

b) Preparation of Homogeneously Cross-linked Anti-digoxin Antibody

The preparation of the homogeneously cross-linked anti-digoxin antibody takes place in the same way as described for the preparation of homogeneously cross-linked anti-mouse Fcγ antibody (Example 8b)).

Subsequently, test tubes are loaded successively with solutions of the two products.

In the immunoassay, digitoxigenin-labelled antibodies are used. The preparation of such labelled antibodies takes place analogously to Example 9a with digitoxigenin-3-succinimidyl-hydroxysuccinimide ester.

Example 10

A matrix is prepared in that the solid phase is simultaneously incubated with polymer I and II.

A solution consisting of 10 μg/ml poly-streptavidin (preparation according to Example 1d) and 0.1 μg/ml thermo-BSA-biotin (preparation according to Example 1a) in 5 mMol/l. acetic acid is incubated in polystyrene tubes for 20 hours.

After removal of the loading solution, it is afterloaded with 10 mMol/l potassium phosphate buffer, pH 7⅛ g BSA (30 minutes) and, after aspiration, is dried.

Example 11 a) Biotinylation of Aminodextran 500

100 mg Aminodextran (m.W. 500,000, 230 NH₂ groups/mole of dextran) are dissolved in 5 ml 100 mM potasssium phosphate buffer, pH 8.5. To this are added 90 μl of a solution of 10 mg biotin-N-hydroxysuccinimide ester (biotin-OSu) in 1 ml dimethyl sulphoxide (DMSO), slowly while stirring.

After 2 hours at room temperature, the reaction is stopped with 50 μl of 200 mMol/l lysine HCl, pH 8.5.

Subsequently, the batch is dialysed twice against the 500 fold volume of 50 mMol/l potassium phosphate buffer, pH 7.2 and diluted with 40 mMol/ potassium phosphate buffer, pH 7.0, to a concentration of 10 μg/ml.

b Loading of Polystyrene Tubes with Aminodextran Biotin

In each case, 1.5 ml of this loading solution are filled into polystyrene test tubes and incubated at room temperature for 6 hours.

Subsequently, this is filtered off with suction, 1.5 ml of a homogeneously or heterogeneously cross-linked polystreptavidin (Example 1 or 2) added thereto and incubated overnight. Thereafter, the test tubes are completely emptied and used for the appropriate test.

Example 12

Thermo-BSA-streptavidin tubes, produced according to EP-A 269,092, are incubated for 20 hours with 10 μ/ml thermo-BSA-biotin solution (preparation according to Example 1a) in 50 mMol/l potassium phosphate, pH 7.2.

After complete removal of the solution, 1.5 ml polystreptavidin solution (according to Example 1 or 2) is added thereto and incubated overnight at room temperature. Thereafter, the test tubes are completely emptied and used for the appropriate test.

Example 13 a) Biotinylation of Poly(Lys/Phe)

100 mg Poly(Lys/Phe) HBr (hydrobromide of a copolymer of lysine and phenylalanine (L-Lys-L-Phe 1:1, M.W. 46 KD, manufacturer Sigma) are dissolved in 25 ml H₂O.

180 μl of a solution of 5 mg biotin-OSu in 1 ml. DMSO are slowly added thereto, while stirring, whereby the pH is kept constant of 8.0 by means of an autotitrator.

After 2 hours at room temperature, the reaction is stopped with 50 μl. 200 mMol/l lysine HCl, pH 8.5.

Subsequently, the batch is dialysed twice against the 500 fold volume of bidist. H₂O and diluted to a concentration of 10 μg/ml.

b) Loading of Polystyrene Tubes with Poly/Phe/Lys)-biotin

In each case 1.5 ml of this loading solution are filled into γ-irradiated polystyrene test tubes and incubated at room temperature for 6 hours. Subsequent thereto, this is removed and 1.5 ml polystreptavidin solution (preparation according to Example 1 or 2) added thereto and incubated overnight at room temperature. Thereafter, the test tubes are completely emptied and used for the appropriate test.

Example 14

A matrix is prepared consisting of a thermo-BSA-biotin conjugate as a polymer I and a heterogeneously cross-linked conjugate of streptavidin and anti-digoxin antibodies from sheep as polymer II.

a) Preparation of Thermo-BSA-biotin

The preparation takes place as described under Example 1a). In the matrix according to the invention, the thermo-BSA-biotin complex represents the polymer I.

b) Preparation of Mixed Polymer of Streptavidin and Anti-digoxin Antibodies from Sheep 30 mg Streptavidin are activated as described under Example 1c) with S-acetylmercaptosuccinic acid anhydride (SAMBA).

At the same time, 30 mg anti-digoxin antibodies are activated in the same way with maleimidiohexanoyl-N-hydroxysuccinimide ester (MHS), as is described in Example 1b) for the MHS-activation of streptavidin. For the reaction, a fivefold molar excess of MHS (dissolved in DMSO) with regard to the antibodies are used.

The conjugation of activated SAMBA-streptavidin with activated MHS antibodies takes place in the same way as is described for the homogeneous cross-linking of streptavidin in Example 1d).

The streptavidin-antibody conjugate obtained in this way can be applied to the solid phase, either directly or after gel filtration and renewed concentration, for the adsorption. In the matrix according to the invention, it represents the polymer II.

For the preparation of the matrix according to the invention, the test tubes are coated either successively with solution of the two products or, simultaneously as described in Example 10 in the presence of 5 mMol/l acetic acid.

Digitoxigenin-labelled antibodies are used in the immunoassay. The preparation of such labelled antibodies takes place analogously to Example 9a with digitoxigenin-3-succinimidylhydroxysuccinimide ester.

We claim:

1. Process for the production of a solid phase matrix of an insoluble carrier with a specifically bindable substance bound thereto, comprising:
   (i) coating a substance on an insoluble carrier material, wherein said substance contains a first polymer, said first polymer is a protein polymer comprising hydrophobic protein molecules having a molecular weight of from 10,000 to 700,000 which have been cross-linked with a bifunctional or polyfunctional compound to produce said protein polymer, and a plurality of molecules of a first member of a specific binding pair P1, and
   (ii) cross linking said first polymer to a second polymer which comprises a plurality of molecules of a second member of a specific binding pair P2, and binding sites for a complex of an immune component and an analyte, wherein said substance and said second polymer are cross linked via binding of P1 and P2 to each other, wherein said first polymer is more hydrophobic than said second polymer.

2. Process of claim 1, wherein said protein is a soluble protein having a molecular weight above about 200,000 and is more hydrophobic than both $P_1$ and $P_2$.

3. Process of claim 1, wherein said protein polymer has a molecular weight of from 200,000 to 20,000,000.

4. Process of claim 1, wherein said bifunctional compound is disuccinimidyl suberate.

5. Process of claim 1, wherein said protein is bovine serum albumin or immune-gamma globulin.

6. Process of claim 1, wherein said second polymer consists of cross-linked molecules of $P_2$ and a homo-, heterobi- or polyfunctional linker.

7. Process of claim 1, wherein said second polymer consists of molecules of $P_2$.

8. Process of claim 1, wherein said second polymer comprises a second component cross-linked with $P_2$.

9. Process of claim 1, wherein said second polymer comprises a hydrophobic protein.

10. Process of claim 1, wherein said second polymer comprises a hydrophobic protein cross-linked to $P_2$.

11. Process of claim 1, wherein the specific binding pair of $P_1$–$P_2$ is selected from the group consisting of biotin-avidin, biotin-streptavidin, antigen-antibody, hapten-antibody, protein A-immune-γ-globulin.

12. Process according to claim 1, wherein said insoluble solid carrier is furan, glass, titanium, dioxide, polystyrene, γ-globulin activated polystyrene, paper, or polyolefin.

13. Solid matrix useful in determining an analyte in a sample prepared by the process of claim 1.

* * * * *